United States Patent [19]

Vicenzi et al.

[11] 4,302,640
[45] Nov. 24, 1981

[54] FLOW DETECTOR

[75] Inventors: Reno L. Vicenzi, Riverside; Paul R. Smargiassi, Vacaville, both of Calif.

[73] Assignee: Bourns Medical Systems, Inc., Riverside, Calif.

[21] Appl. No.: 91,925

[22] Filed: Nov. 7, 1979

[51] Int. Cl.³ ............................................ H01H 35/34
[52] U.S. Cl. ................................. 200/81 R; 137/557; 128/202.22; 200/81.9 R; 200/83 Q; 200/83 R; 340/605; 340/611
[58] Field of Search ...................... 340/605, 606, 611; 137/312, 557, 551; 128/202.22, 207.15, 204.24, 205.23, 205.17, 204.21; 200/81 R, 83 R, 81.9 R, 83 Q

[56] References Cited

U.S. PATENT DOCUMENTS

| | | | |
|---|---|---|---|
| 3,867,934 | 2/1975 | Ollivier | 128/202.22 |
| 3,870,012 | 3/1975 | Metivier | 128/202.22 X |
| 4,067,329 | 1/1978 | Winicki | 340/605 X |
| 4,176,617 | 12/1979 | Pilipski | 128/202.22 X |

Primary Examiner—John W. Caldwell, Sr.
Assistant Examiner—Daniel Myer

[57] ABSTRACT

A flow detector including an orifice for forming a vena contracta to activate a connected pressure detector so as to trigger an alarm mechanism upon the occurrence of disconnect of the patient exhalation valve in a mechanical ventilator system. A configuration of the flow detector makes erroneous hookup of the ventilator and pressure detector hoses all but impossible.

8 Claims, 3 Drawing Figures

FLOW DETECTOR

BACKGROUND OF THE INVENTION

1. Field of the Invention

The present invention relates to flow detection devices and more particularly to a detector for providing a warning in the event of an exhalation valve line disconnect in a mechanical ventilator system.

2. Description of the Prior Art

Pressure monitors have long been used in the exhalation lines of mechanical ventilators and the art associated with such use is well-known. In some systems, delivery of air to the patient is largely controlled by the exhalation valve. Thus, closure of the exhalation valve allows breathing gas to flow to the patient, while opening of the exhalation valve allows the patient to exhale to atmosphere. In many systems, the exhalation valve is pressure actuated and therefore, is closed by pressurized gas from the ventilator or other source. It is important that a disconnection in the pressurizing line for the exhalation valve be promptly discovered and rectified. This is normally done by using a pressure detector in the pressurizing system. A disconnect occurring between the ventilator and the pressure detector is readily discovered by prior art monitor and warning systems because of the almost instantaneous pressure drop to the pressure detector. A disconnect occurring downstream of the pressure detector may be more difficult to sense because back pressures may develop which will maintain the pressure detector in the pressure sensing mode, thus, a disconnect occurring in this part of the ventilator may go unnoticed. Thus, some of these prior art pressure monitoring devices have served a somewhat narrow purpose and have met special needs as presented by specific problems but have not met nor solved the problem of a disconnect occurring downstream of the pressure detector as described. Some of these prior art devices have been described in the following listed patents that were brought to the attention of the applicant through a novelty search conducted in the U.S. Patent and Trademark office:

| Patent No. | Title | Inventor |
| --- | --- | --- |
| 859,147 | "Automatic Alarm Device" | Strodtbeck |
| 3,595,228 | "Flow Line Break Alarm Device" | Simon |
| 3,870,012 | "Pressure Drop Alarm Device" | Metivier |
| 2,854,001 | "Breathing Apparatus" | Humblet |
| 3,952,773 | "Breathing Gas Supply Controller" | Hahn |
| 4,054,133 | "Control for a Demand Cannula" | Myers |
| 2,376,348 | "Resuscitator" | Fox |
| 2,408,136 | "Resuscitator-Insufflator-Aspirator" | Fox |
| 2,547,458 | "Resuscitator" | Goodner |
| 2,881,757 | "Respirator Control Systems" | Haverland |
| 3,046,979 | "Lung Ventilators and Control Mechanism Therefor" | Andreasen |
| 3,073,298 | "Respiratory Device" | Stanton |
| 3,319,627 | "Intermittent Positive Pressure Breathing Apparatus" | Windsor |
| 3,385,295 | "Apparatus for use in Administering Intermittent Positive Pressure Breathing Therapy" | Beasley |
| 3,485,243 | "Respirator with Improved Exhalation Valve and Control Means" | Bird et al |
| 3,542,020 | "Fluid Flow Devices" | Bushman |
| 3,630,196 | "Manual Positive Pressure Breathing Device" | Bird |
| 3,867,934 | "Pressure Monitor for a Lung Ventilator" | Ollivier |
| 3,903,881 | "Respirator System and Method" | Weigl |
| 3,915,164 | "Ventilator" | Bird |
| 3,974,828 | "Ventilator and Method" | Bird |
| 4,044,763 | "Ventilator and Method" | Bird |
| 4,067,329 | "Tube Disconnection Warning Device" | Winicki |

Many of these prior art devices have had defects which have made them inappropriate and possibly dangerous. In some cases, they have been unreliable, difficult to control and inaccurate and, therefore, the quest for an improved disconnect sensor has continued.

It would, therefore, be a great advantage to the art to provide flow sensing means, operable to sense the pressure change resulting from disconnect in the exhalation valve pressurizing system, especially when such disconnect occurs downstream from the system pressure monitor.

It would be a further great advantage to provide such sensing means in a form easily adaptable to existing systems.

A further significant advantage would be realized if such sensing means could be provided in a convenient and economical form with little chance for installation error.

SUMMARY OF THE INVENTION

In view of the above-stated desirable advantages, it is therefore an object of the present invention to provide a flow detector, operable to sense a disconnect in the pressurizing line for the exhalation valve in a mechanical ventilator system when such disconnect occurs downstream from a system pressure monitor.

It is a further object of the present invention to provide such a detector in a form easily adaptable to existing systems.

It is an additional significant object of the instant invention to provide the advantages of the detector contemplated in a convenient and economical form that may be utilized in the modification of existing systems with little chance for installation error.

To realize the above-stated objects, the subject invention provides a flow detector inserted in a fluid pressure line from a pressurized source (such as a ventilator) to a pressure actuated exhalation valve. This detector consists of an orifice in the fluid pressure line, a chamber immediately downstream of the orifice and a pressure sensing means for providing a signal when the pressure in the chamber decreases below a preset value.

BRIEF DESCRIPTION OF THE DRAWINGS

Further advantages and features of the present invention will be more fully apparent to those skilled in the art to which the invention pertains from the ensuing detailed description thereof, regarded in conjunction with the accompanying drawings, wherein like reference characters refer to like parts throughout and in which.

DETAILED DESCRIPTION

Although specific embodiments of the invention will now be described with reference to the drawings, it should be understood that such embodiments are by way of example only and merely illustrative of but a small number of the many possible specific embodiments which can represent applications of the principles of the invention. Various changes and modifications obvious to one skilled in the art to which the invention pertains are deemed to be within the spirit, scope and contemplation of the invention as further defined in the appended claims.

Figure 1:
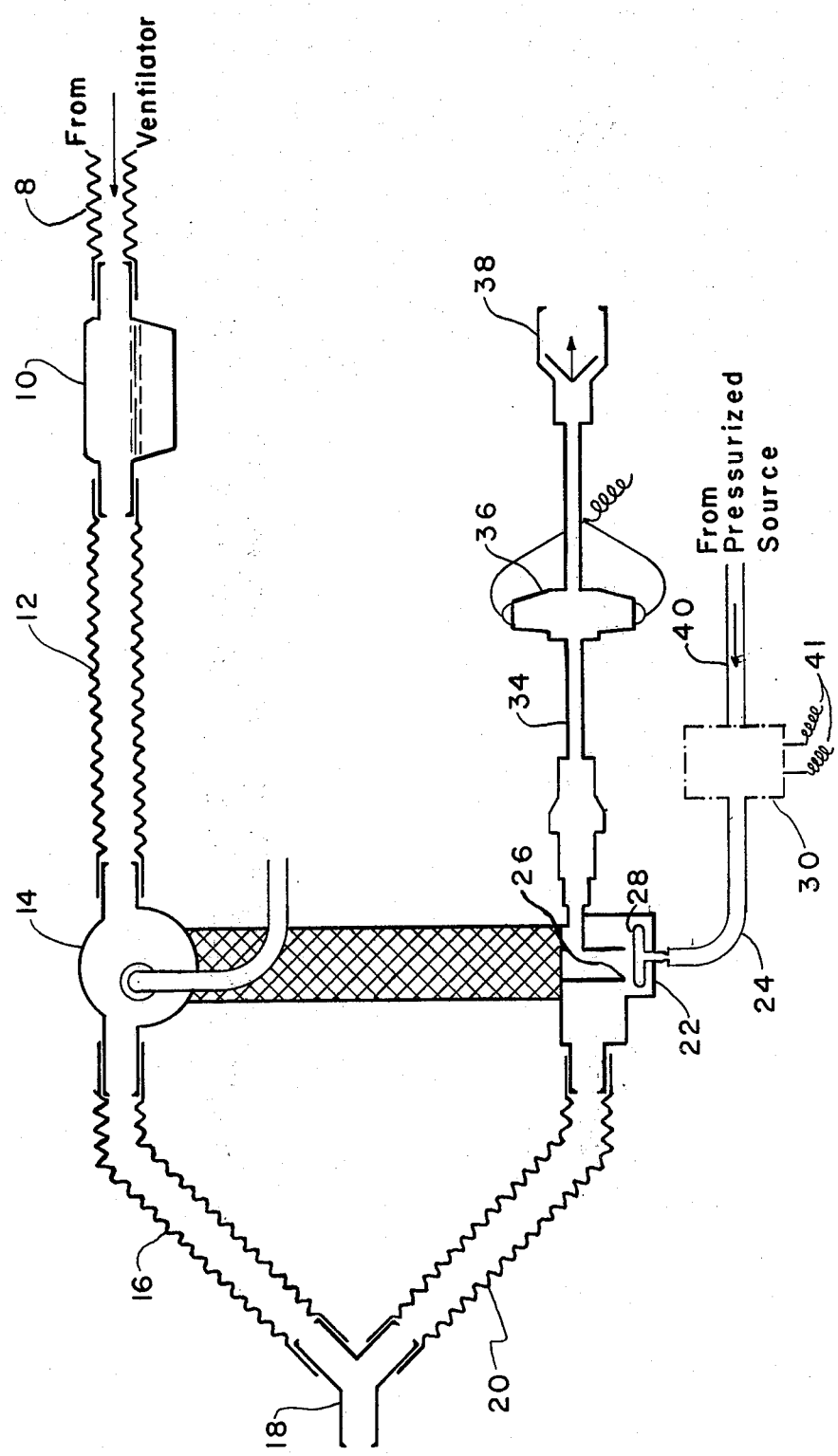
FIG. 1 is an idealized schematic illustrating the incorporation of a flow detection device of the subject invention into the system of a modern mechanical ventilator.

Referring to FIG. 1 with greater particularity, a partial, idealized schematic illustrates the general operation of a portion of a typical modern ventilator utilizing the advantages of the invention. Tubing 8 supplies pressurized gas from a ventilator (not shown) to a humidifier 10 which humidifies the breathing gas in a conventional manner and delivers it to nebulizer 14 by way of tubing 12. The humidified and treated gas then flows through tubing 16 to a patient adapter 18 from which the gas is delivered to the patient. During the inspiratory portion of a breathing cycle an exhalation valve 22 is closed.

During the expiratory portion of the breathing cycle, exhalation valve 22, now in the open state, receives the expiratory gas by way of exhalation tubing 20. Expiratory gas continues through flow tube 34, flow sensor 36 and normally to atmosphere by way of an exhalation check valve 38.

In most modern ventilator systems, delivery of breathing gas to the patient is controlled primarily by the operation of the exhalation valve 22. For a patient to receive the prescribed breathing gases, the exhalation valve must be in a closed state. Typically, the exhalation valve 22 in such a system has a pressure actuated valve closure member 28 which, when pressurized, is forced against its valve seat 26 so as to close the exhalation valve and direct breathing gas to flow to the patient. Pressure actuated valve member 28 typically may be a valve balloon such as shown, a diaphragm, or any other type of pressure actuated valve member.

When valve member 28 is not pressurized, it is displaced from its valve seat 26 thereby opening the exhalation valve and allowing expiratory gas from the patient to flow out through the exhalation valve.

Therefore, during the inspiration phase of a breathing cycle, a pressurized gas from the ventilator or another pressure source (not shown) is supplied to the valve member 28. Gas from the pressurized gas source flows through a conduit 40 into a flow detector 30 and out through connecting conduit 24 to valve member 28. In accordance with the present invention, flow detector 30 provides an output signal via electrical output leads 41 indicative of a loss of pressurization of the valve member 28. Two embodiments of flow detector 30 in accordance with the subject invention are more particularly described in regard to FIGS. 2 and 3.

The basic purpose of flow detector 30 is to provide an output signal which can be used to indicate that there is insufficient pressure to activate valve member 28 during the inspiration portion of the breathing cycle and, therefore, a problem condition exists in that a patient may not be receiving a machine breath.

In the prior art, a pressure sensor such as a transducer or a pressure switch would be used to sense the pressure in the tube running from the ventilator to the valve closure member. If a disconnect or a leak occurred upstream of the pressure sensor, it is clear that the pressure sensor would see a lower pressure than desired and would provide the appropriate indication of a problem. However, if a leak or disconnect occurred downstream of the pressure sensing device, it is possible that there would be a sufficient flow of gas from the ventilator to keep the pressure sensor pressurized and therefore, inhibited from giving an indication of a lower pressure, i.e., a problem condition. The flow detector 30 of the subject invention provides a suitable output signal indicative of an appropriate pressure loss regardless of whether the leak or disconnect occurs upstream or downstream of the detector. It should be noted that depending on whether a pressure transducer or pressure switch is utilized, the output indicating a problem condition can either be a signal whose value varies proportionally to the pressure being sensed or can be the opening or closing of a switch to indicate that the pressure has dropped below a preset value.

Figure 2:
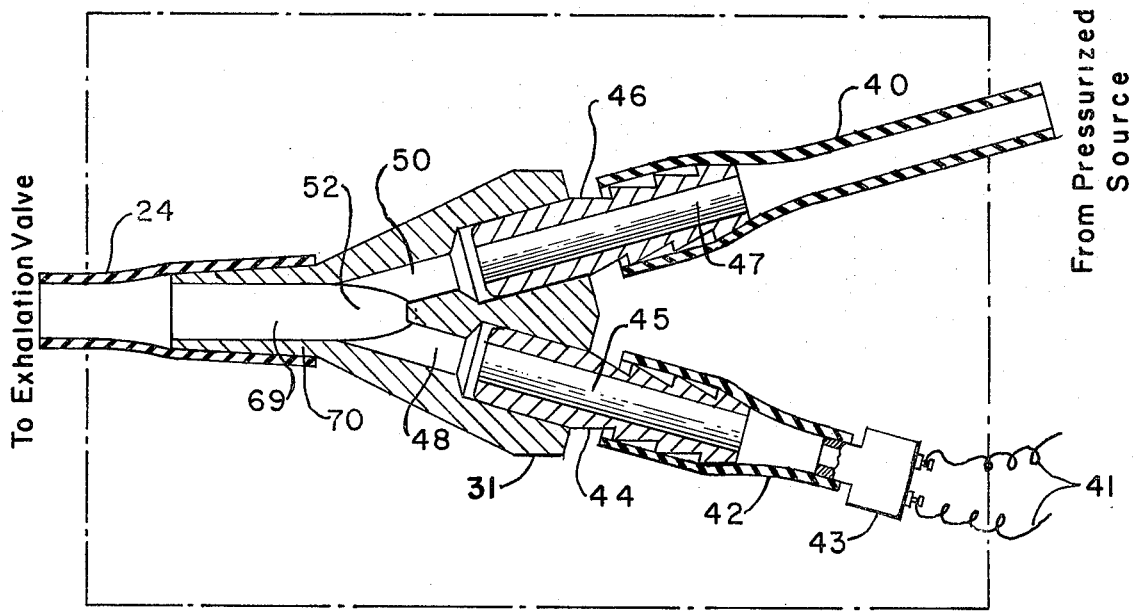
FIG. 2 is an idealized cross-sectional view of one embodiment of the subject invention.

FIG. 2 shows a first embodiment of flow detector 30 in accordance with the subject invention. This embodiment is particularly suitable for adding on to existing ventilator equipment.

Flow detector 30 is basically comprised of a three-legged flow adapter 31 having two input legs 44, 46 and one output leg 70 and a pressure sensor 43 connected to adapter 31 at one of the input legs by means of a pressure sensing tube 42. In the preferred form of adapter 31, the two input legs 44, 46 are identical and each input leg includes a passageway 45, 47 and a substantially identical orifice 48, 50, respectively. These passageways 45, 47 merge together at a chamber 52 just downstream of orifices 48, 50. Chamber 52 forms the upstream end of passageway 69 of a third leg 70 of adapter 31. Passageway 47 of input leg 46 is connected to a source of pressurized gas, such as a ventilator, by means of tubing 40. Passageway 69 of output leg 70 is connected to valve closure member 28 by means of connecting tube 24.

Pressure sensor 43 serves to sense the pressure in chamber 52 and provides an electrical output via output leads 41 which either may vary in accordance with the pressure detected within chamber 52 (if sensor 43 is a transducer), or may alternatively (if sensor 43 is a pressure switch) provide an open or closed circuit condition via leads 41, depending on whether the pressure in chamber 52 is or is not below a predetermined pressure level.

In normal operation, when exhalation valve 22 is desired to be closed, a pressurized gas source is applied to tube 40 so as to build up a pressure within the lines connecting it to the valve member 28. Under normal circumstances where there is no leak or disconnect, a minimal amount of gas flows through adapter 31 (only enough to fill the tubes, etc.) and a pressure above atmospheric is maintained throughout the pressurizing system, including member 52. Under such circumstances pressure sensor 43 does not provide an output signal indicative of a problem. However, if a disconnect or substantial leak occurs upstream of input passageway 47, all or a substantial part of the pressurized gas will leak out and not reach input leg 46. In such a situation, chamber 52 effectively is vented to the atmosphere and pressure sensor 43 will sense that the pressure in chamber 52 is below that desired and provide an output signal indicative thereof. Preferably, such an output signal will be used to initiate an alarm of a problem condition.

Obviously, if a disconnect or leak occurs between the pressure sensor 43 and leg 44, a similar result will occur.

However, if a leak or disconnect occurs downstream of adapter 31, chamber 52 will not be vented to atmosphere but rather a substantial pressurized gas flow will take place from the ventilator through passageway 47 and orifice 50. Such a flow will form a vena contracta (i.e., a low pressure region) within chamber 52. As in the other above-mentioned problem situations, sensor 43 will detect a lower pressure than desired in chamber 52 and will provide an output signal indicative of a problem condition.

Therefore, no matter where a leak or disconnect may occur in the exhalation valve pressurizing system between the source of pressurized gas and the valve member to be actuated, the flow detector 30 of the subject invention will provide an output signal indicative thereof.

As stated above in the preferred version of this embodiment, both input legs 44 and 46 are identical, each having identical orifices. While it is not necessary for the leg that is connected to the pressure sensor 43 to have an orifice therein for it to function properly, by making both legs identical the passageway of either leg can be connected to the source of pressurized gas and the passageway of the other leg can be connected to the pressure sensor 43. In this way it is practically impossible for the inputs to the adapter to be hooked up improperly. It should also be noted that the three legs must be oriented such that the input leg connected from the source of pressurized gas is substantially aligned with the output leg to receive the full gas flow and the other leg connected to the pressure sensor is substantially nonaligned so that the gas flow does not serve to pressurize this other leg. Normally this means that the angle between the center line of the passageway through the input leg connected to the pressure source and the input leg connected to the pressure sensor 43 must be no more than 90 degrees.

Figure 3:
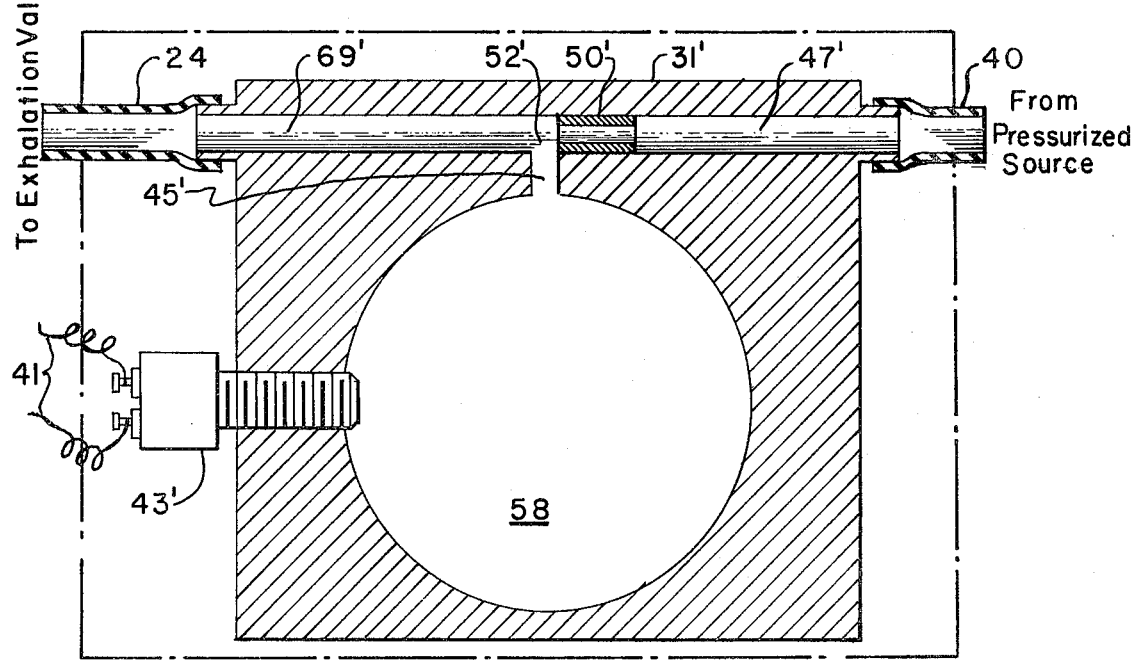
FIG. 3 is an idealized cross-sectional view of another embodiment contemplated by the subject invention.

In FIG. 3 a slightly different embodiment of the subject invention is shown. This embodiment is particularly suitable where it is desired that the flow detector be incorporated into the exhalation valve or into the ventilator itself.

In this embodiment, tubing 40 from a pressurized gas source (not shown) is connected to a passageway 47' in a flow detector member 31'. An orifice 50' is located in passageway 47'. Immediately downstream of orifice 50' is a pressure chamber 52' which forms the upstream end of an output passageway 69'. This passageway 69' is substantially aligned with passageway 47' and serves to direct the flow of gases from passageway 47' out of the flow detector into connector tube 24 which is then connected to pressure actuated valve member 28 of exhalation valve 22 (see FIG. 1). A passageway 45' extends from pressure chamber 52' to a pressure detector cavity 58 to which a pressure sensor 43' is connected. Pressure sensor 43' has electrical output leads 41 which are used to provide an output signal indicative of a problem situation.

Flow detector 30' operates substantially the same as flow detector 30 described above in regard to FIG. 2 in that a leak or disconnection occurring either upstream or downstream from detector member 31' will cause the pressure in pressure chamber 52' to be either at or below atmosphere. On sensing such a condition, pressure sensor 43' will provide an output signal indicative of such a problem situation.

In this embodiment, it is possible that the entire flow detector can be integrated into a pressure sensor wherein pressure detector cavity 58 would be directly exposed to a pressure responsive member of a sensor such as a diaphragm.

This embodiment could also be readily incorporated into a ventilator device itself, which would permit the use of a single tube from the flow detector output portion of the ventilator to the exhalation valve.

Thus there has been described a flow detector that will provide much greater sensitivity and reliability than has been known in the prior art. In one embodiment, it is simple and easy to install in existing systems with a minimal chance of installation error because of its symmetrical configuration.

It is here pointed out that although the present invention has been shown and described with reference to the particular embodiments described herein, nevertheless, various changes and modifications obvious to one skilled in the art to which the invention pertains are deemed to be within the purview of the invention.

What is claimed and desired to be secured by Letters Patent of the United Stats is:

1. In a system for actuating an exhalation valve for use in respiratory therapy comprised of a source of pressurized gas, a gas pressure actuated valve closure member, a valve seat for the valve member, means connecting the pressurized gas source to the valve closure member and a detector coupled to the connecting means for detecting leaks, the improvement comprising the use of an improved flow detector coupled inline between upstream and downstream portions of the connecting means for providing an output signal when there is insufficient pressure to force the gas pressure actuated valve closure member against its valve seat during the inspiration portion of a breathing cycle, said improved flow detector including:

a chamber coupled to the connecting means, said chamber being normally pressurized by gas from the gas source at a pressure substantially determined by the gas source;

first low pressure generating means coupled inline between said upstream and downstream portions of the connecting means and located immediately upstream of said chamber, said low pressure generating means being responsive to the flow of gas therethrough from the pressurized gas source due to a leak or disconnect in said downstream portion of the connecting means for causing the pressure in said chamber to decrease below a predetermined value; and pressure sensing means coupled to said chamber for providing a predetermined output signal when the pressure in said chamber decreases below the predetermined value.

2. A flow detector as in claim 1 wherein said first low pressure generating means defines a first orifice.

3. A flow detector as in claim 1, further including:

a first leg including an input passageway having upstream and downstream ends, said upstream end of said input passageway being coupled via said upstream portion of the connecting means to the pressurized gas source, said first low pressure generating means being located at said downstream end of said input passageway;

a second leg including an outlet passageway having upstream and downstream ends, said chamber being located at said upstream end of said outlet passageway, said downstream end of said outlet passageway being coupled via said downstream portion of the connecting means to the gas pressure actuated valve closure member; and a third leg having a pressure sensing passageway, said pressure sensing passageway connecting said chamber to said pressure sensing means.

4. A detector as in claim 3 wherein said input and pressure sensing passageways have centerlines respectively passing therethrough, said centerlines intersecting with each other to form an angle therebetween which is no more than 90 degrees.

5. A detector as in claim 4 wherein said pressure sensing passageway includes second low pressure generating means, said pressure sensing and input passageways being substantially identical to each other, said first and third legs being adapted for connection to the connecting means.

6. A detector as in claim 5 wherein said input, pressure sensing and output passageways form a "Y" shaped structure with the centerlines of said input passageway and said pressure sensing passageway intersecting the centerline of said output passageway at the same symmetrical acute angle.

7. A detector as in claim 1 wherein said pressure sensing means is a pressure switch which provides a predetermined output signal when the pressure sensed in said chamber is less than the predetermined value.

8. A flow detector for use in detecting leaks and disconnects in a system for pressuring a pressure activated exhalation valve closure member by pressurized gas from a gas pressure source, said flow detector comprising:

an input passageway for receiving pressurized gas from the gas pressure source;

orifice means coupled to said input passageway;

an output passageway coupled between said orifice means and the pressure activated exhalation valve closure member, for providing a path for the pressurized gas between said orifice means and the exhalation valve closure member, said output passageway including chamber means located immediately downstream from said orifice means said chamber means being normally pressurized by gas from the gas pressure source at a pressure substantially determined by the gas pressure source, said orifice means being responsive to the flow of gas therethrough due to a leak or disconnect in the system between said chamber means and the pressure activated exhalation valve closure member for causing the pressure in said chamber means to decrease below a predetermined value; and sensor means, connected to said chamber means, for sensing the gas pressure within said chamber means and providing a predetermined output signal when the pressure in said chamber means is below the predetermined value.

* * * * *

UNITED STATES PATENT OFFICE
CERTIFICATE OF CORRECTION

Patent No. 4,302,640            Dated November 24, 1981

Inventor(s) Reno L. Vicenzi and Paul R. Smargiassi

It is certified that error appears in the above-identified patent and that said Letters Patent are hereby corrected as shown below:

Column 4, line 58, "member" should read --chamber--

Signed and Sealed this

Twenty-third Day of February 1982

[SEAL]

Attest:

Attesting Officer

GERALD J. MOSSINGHOFF

Commissioner of Patents and Trademarks